US005091954A

United States Patent [19]

Sasaki et al.

[11] Patent Number: 5,091,954

[45] Date of Patent: Feb. 25, 1992

[54] NOISE REDUCING RECEIVER DEVICE

[75] Inventors: Tooru Sasaki; Masashi Ohkubo, both of Tokyo; Akira Kimura, Kanagawa, all of Japan

[73] Assignee: Sony Corporation, Tokyo, Japan

[21] Appl. No.: 482,250

[22] Filed: Feb. 20, 1990

[30] Foreign Application Priority Data

| | | | |
|---|---|---|---|
| Mar. 1, 1989 | [JP] | Japan | 1-46592 |
| Mar. 1, 1989 | [JP] | Japan | 1-46593 |
| Mar. 6, 1989 | [JP] | Japan | 1-52148 |
| Mar. 6, 1989 | [JP] | Japan | 1-52149 |

[51] Int. Cl.[5] ........ A61F 11/02; H03B 29/00

[52] U.S. Cl. ........ 381/72; 381/71

[58] Field of Search ........ 381/71, 72

[56] References Cited

U.S. PATENT DOCUMENTS

| | | | |
|---|---|---|---|
| 4,455,675 | 6/1984 | Bose et al. | 381/74 |
| 4,494,074 | 1/1985 | Bose . | |
| 4,815,139 | 3/1989 | Eriksson et al. | 381/71 |

FOREIGN PATENT DOCUMENTS

| | | |
|---|---|---|
| 212840 | 3/1987 | European Pat. Off. . |
| 8705430 | 9/1987 | World Int. Prop. O. . |
| 8900746 | 1/1989 | World Int. Prop. O. . |

*Primary Examiner*—Forester W. Isen

*Attorney, Agent, or Firm*—Alvin Sinderbrand; William S. Frommer

[57] ABSTRACT

The present invention is concerned with a receiver device for converting electrical signal from a headphone, a telephone receiver or the like into acoustic signals. More particularly, it relates to a noise reducing receiver device in which acoustic signals in the vicinity of an electro-acoustic transducer element are converted by a microphone into electrical signals and negatively fed back to an amplifier circuit which is adapted for amplifying input electrical signals and supplying the amplified signals to the electro-acoustic transducer element. In the noise reducing receiver device, the input electrical signals are amplified by the amplifier circuit and converted by the electro-acoustic transducer element into output acoustic signals. A microphone is arranged in the vicinity of the electro-acoustic transducer element and adapted for converting the output acoustic signals and external noise into electrical signals, which are negatively fed back to the amplifier circuit via a feedback circuit. The output acoustic signals may be heard at a desired noise reduction level by adjusting the transfer function H of the electro-acoustic transducer element, the transfer function A of the amplifier circuit, the transfer function M of the microphone and the transfer function $\beta$ of the feedback circuit within a range determined by $|AHM\beta| >> 1$.

7 Claims, 3 Drawing Sheets

NOISE REDUCING RECEIVER DEVICE

BACKGROUND OF THE INVENTION

1. Field of the Invention

This invention relates to an active noise reducing receiver device for converting electrical signals into output acoustic signals. More particularly, it relates to a noise reducing receiver device in which acoustic signals in the vicinity of an electro-acoustic transducer element are converted by a microphone into electrical signals and negatively fed back for noise reduction to an amplifier circuit which is adapted for amplifying input electrical signals and supplying the amplified signals to the electro-acoustic transducer element.

2. Prior Art

Headphone devices in the form of a receiver utilizing only an electro-acoustic transducer element attached to the listener's ear used extensively.

However, with such passive type headphone devices, not only the acoustic output, but also surrounding noise is input to the listener's ear. For this reason, a so-called active type noise-reducing headphone device has recently been proposed, as disclosed for example in U.S. Pat. Nos. 4,455,675 and 4,494,074, according to which the noise in the vicinity of the headphone unit is reduced by a negative feedback loop, by means of which output acoustic signals in the vicinity of the headphone unit which is adapted to output acoustic signals, converted from electrical signals are converted into electrical signals and fed back in an antiphase relation to the input electrical signals.

Referring to FIG. 1, in which the basic construction of the above mentioned active type noise reducing headphone device is illustrated, a microphone unit 6 is provided in the vicinity of a headphone unit 4 attached to a listener's ear 20, and a signal synthesizer 2 is provided at an input side of an amplifier 3 which is adapted for amplifying an input electrical signal S applied from a signal source 10 to a signal input terminal 1 before supplying the signal to the headphone unit 4. The acoustic signals in the vicinity of the headphone unit 4 are converted by the microphone unit 6 into electrical signals which are supplied via feedback circuit 7 to the signal synthesizer 2 where the input electrical signal S and feedback signals output from the feedback circuit 7 are summed together before being supplied to the amplifier 3 as negative feedback.

As in the above described active type noise reducing headphone device, the noise level in the acoustic signal input to the listener's ear 20 may be reduced by summing acoustic output signals from the headphone unit 4 and noise signals from the vicinity of the the acoustic meatus of the listener's ear 20 to produce an acoustic signal, converting the acoustic signal by means of the microphone unit 6 into an electrical signal and negatively feeding back the electrical signal via feedback circuit 7 to the input side of the amplifier 3.

In the conventional passive type headphone device, its frequency characteristics are monistically determined by the size or the weight of the diaphragm of the headphone unit, the impedance characteristics of the voice coil or the acoustic circuit around the diaphragm of the headphone unit. The frequency characteristics can only be corrected by gradually changing various factors influencing the frequency characteristics for achieving the desired characteristics. Moreover, distortion caused by the magnetic circuits or due to mechanical nonlinearities, such as edges, occur frequently. Above all, distortion predominates at the low range resonant frequency not exceeding $f_0$.

It is noted that, with the use of the active type noise reducing headphone device, whose function is to reduce external noise, too large a noise reduction level may result in a listener hearing a music broadcast while failing to hear another person talking to him or failing to hear an emergency signal. On the other hand, two low a noise reduction level proves to be ineffective in factories or at construction sites with a high noise level.

The conventional active type noise reducing headphone device suffers from the drawback that, since it has fixed characteristics, it cannot be used for certain occasionally desirable noise reduction levels.

The above mentioned conventional active type noise reducing headphone device also has the drawback that, when mechanical vibrations, such as impact vibrations applied to the housing of the headphone device or frictional vibrations of connection cords, are transmitted to the microphone unit, these vibrational noises are converted by the microphone unit into electrical signals, so that external noise cannot be reduced in a regular manner. In other words, the microphone unit, which is adapted for converting the sound pressure into electrical signals, is also responsive to mechanical vibrations to convert mechanical vibration noise into output electrical signals.

SUMMARY OF THE INVENTION

It is an object of the present invention to provide an active type noise reducing receiver device which is adjustable for use at occasionally required noise reduction levels.

It is another object of the present invention to provide a noise reduction receiver device in which the noise reducing level may be changed without affecting the signal level of the acoustic signal output by the electro-acoustic transducer element.

It is further object of the present invention to provide a noise reducing receiver device in which frequency characteristics as well as the noise reduction level may be adjusted to occasionally desirable values.

It is a further object of the present invention to provide a noise reducing receiver device in which the external noise may always be reduced in a regular manner without being influenced by noise caused by mechanical vibrations.

According to the present invention, there is provided a noise reducing receiver device comprising receiving means for receiving an input signal, electro-acoustic transducing means for converting electrical signals into acoustic output signals, amplifying means for amplifying said input signal received by said receiving means to produced an amplified electrical signal, said amplifying means being coupled with an input of said electro-acoustic transducing means to supply said amplified electrical signal thereto, microphone means for converting output acoustic signals of said electro-acoustic transducing means into electrical signals, and feedback means for negatively feeding back electrical signals produced by said microphone means to an input of said amplifying means, wherein said electro-acoustic transducing means, said amplifying means, said microphone means and said feedback means have respective transfer functions H, A, M and $\beta$, at least one of said transfer functions being adjustable within a predetermined range such that $|AHM\beta|>>1$, that is, $|AHM\beta|$ is much greater than 1.

DETAILED DESCRIPTION OF THE INVENTION

Certain preferred embodiments of the present invention are explained herein in detail with reference to the accompanying drawings.

Figure 1:
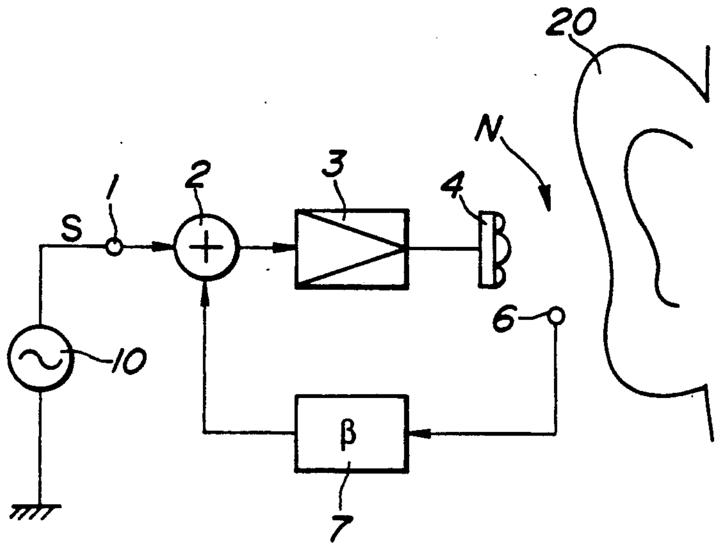
FIG. 1 PRIOR ART
FIG. 1 is a diagrammatic view showing the basic construction of a conventional active type noise reducing receiver.
Figure 2:
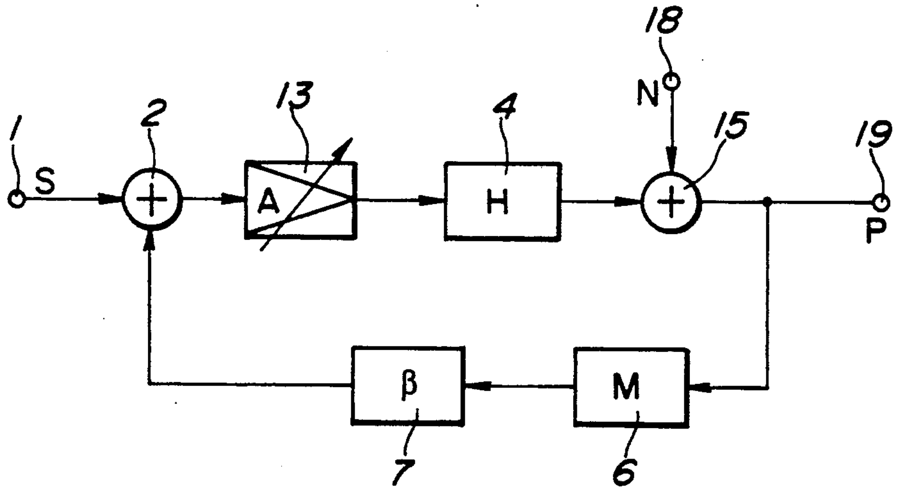
FIGS. 2 to 4 are equivalent block diagrams illustrating various embodiments of an active noise reducing receiver according to the present invention.

In an embodiment shown in the equivalent block diagram of FIG. 2, the present invention is applied to an active type noise reducing headphone device of the type shown in FIG. 1, in which a synthesized output signal from a signal synthesizer 2 is supplied to a headphone unit 4 via a variable gain amplifier 13 having a variable presettable gain A.

The acoustic signal output by the headphone unit 4 is summed with a noise signal N from the environment by an equivalent signal adder 15 in an acoustic space in the vicinity of the headphone unit 4. The synthesized output from the signal adder 15 is supplied via a feedback circuit 7 to the signal synthesizer or adder 2 as the acoustic signal in the vicinity of the headphone unit 4 after conversion into electrical signals by the microphone unit 6.

In the above described headphone device, the transfer function, that is, the gain A, of the aforementioned variable gain amplifier 13, may be preset within a range determined by $AHM\beta>>1$, where H, M, $\beta$ and A denote transfer functions, expressed in the frequency domain, of the headphone unit 4, microphone unit 6, feedback circuit 7 and the variable gain amplifier 13, respectively.

With the use of the above described headphone device, an acoustic signal having a sound pressure level P, where $$P = \frac{AH}{1 + AHM\beta} S + \frac{1}{1 + AHM\beta} \cdot N \qquad (1)$$

is produced at an entrance to the acoustic meatus of the listener's ear (indicated by output terminal 19), to which the headphone device is attached, as a synthesized output from the signal adder 15. In the above formula, S denotes the signal level of an input electrical signal supplied to the signal input terminal 1 and N the signal level of an external noise signal applied to a signal input terminal 18.

As components of the above-described acoustic signal of the sound pressure level P, obtained at signal output terminal 19, the signal level S of the input electrical signal remains constant while $1/M\beta$ is at a constant level, while the signal level N of the external noise is reduced by $1/AHM\beta$. Thus the noise reduction level or the noise signal level N is a function of the gain A of the variable gain amplifier circuit 13 which is variably set within the range of $|AHM\beta|>>1$.

That is, in the headphone device of the present illustrative embodiment, an acoustic signal may be produced at signal output terminal 19, in which, by variably setting the gain A of the variable gain amplifier circuit 13 within the range determined by $|AHM\beta|>>1$, the signal level S of the input electrical signal remains constant, and only the noise level is reduced as a function of the gain A of the variable gain amplifier circuit 13.

Figure 3:
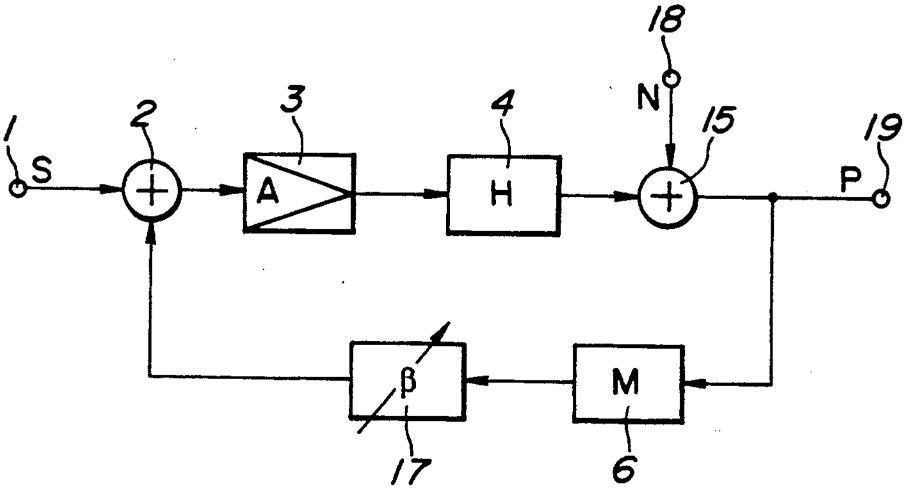

In a further embodiment illustrated by the equivalent block diagram of FIG. 3, the present invention is again applied to an active type noise reducing headphone device of the type described in connection with FIG. 1. In the embodiment of FIG. 3, electrical signals are produced from acoustic signals in the vicinity of the headphone unit 4 by the microphone unit 6 and are supplied via a feedback circuit 17 having a variable presettable transfer function $\beta$ to a signal synthesizer 2 provided at an input side of an amplifier 3 which is adapted for amplifying input electrical signals supplied to a headphone unit 4.

A noise signal N from the environment is added to the acoustic output signal from the headphone unit 4 at an equivalent signal adder 15 in an acoustic space in the vicinity of the headphone unit 4. The synthesized output from the signal adder 15 is supplied via a feedback circuit 17 to the signal adder 2 as the acoustic signal in the vicinity of the headphone unit 4, after conversion into electrical signals by the microphone unit 6.

The feedback circuit 17 in the above headphone device has a phase or frequency characteristic which is able to be variably preset. The transfer function $\beta$ of the feedback circuit 17 in the headphone device may be variably preset within the range determined by $|AHM\beta|>>1$, where A, H and M denote transfer functions, expressed in the frequency domain, of the amplifier 3, headphone unit 4 and the microphone unit 6, respectively.

With the use of the above described headphone device, an acoustic signal having the sound pressure level P, expressed by the formula (1), may similarly be produced at a signal output terminal 19 placed at the entrance to the acoustic meatus of the listener's ear.

With the acoustic signal of the sound pressure level P, obtained at signal output terminal 19, conversion characteristics equal to $1/M\beta$ are afforded for the input electrical signal S, as a function of the transfer function of the feedback circuit 17, which is variably set within the range determined by $|AHM\beta|>>1$, to compensate for frequency characteristics or distortions, while the signal level N of the external noise is reduced by $1/AHM\beta$.

That is, with the use of the headphone device of the present illustrative embodiment, an acoustic signal may be produced at signal output terminal 19, in which, by variably setting the transfer function $\beta$ of the feedback circuit 17 within the range determined by $|AHM\beta|>>1$ as a function of external noise, conversion characteristics equal to $1/M\beta$ are afforded to the input electrical signals to compensate for frequency characteristics or distortion, while the signal level is reduced.

Figure 4:
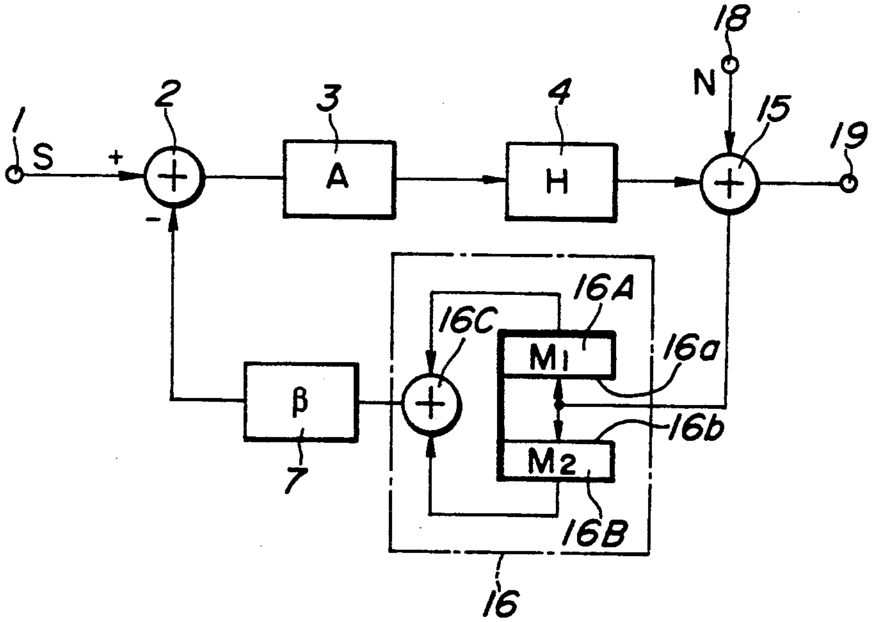

In an embodiment shown by an equivalent circuit diagram of FIG. 4, the present invention is applied to an active noise-reducing headphone device of the type shown in FIG. 1. In lieu of the microphone device 6 adapted to convert acoustic signals in the vicinity of the microphone device 4 into electrical signals, a microphone device 16 including a pair of microphone units 16A, 16B having their diaphragms 16*a*, 16*b* opposing each other by a short distance, is employed. The electrical signals produced at the microphone units 16A, 16B are summed together at a signal adder 16C so as to be output via feedback circuit 7 to a signal adder 2 provided at the input side of an amplifier 3 which is adapted to amplify input electrical signals supplied to the headphone unit 4.

The acoustic output signal from the headphone unit 4 is added with a noise signal N from the environment at an equivalent signal adder 15 in an acoustic space in the vicinity of the headphone unit 4. The synthesized output from the signal adder 15 is supplied via a feedback circuit 7 to the signal adder 2 as the acoustic signal in the vicinity of the headphone unit 4 after conversion into electrical signals by the microphone device 16.

Figure 5:
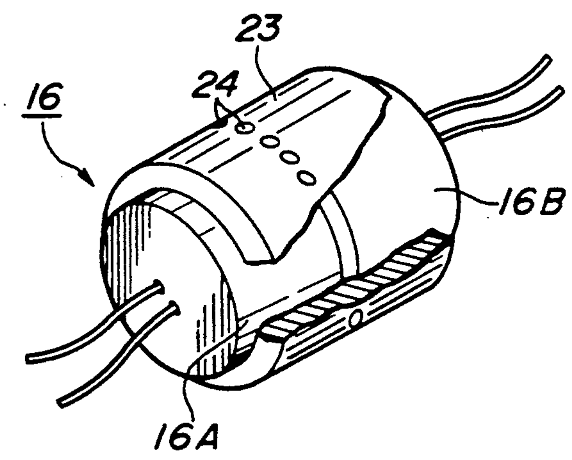
FIG. 5 is a perspective view, partially broken away, showing a specific example of a microphone device of the embodiment of FIG. 4.
Figure 6:
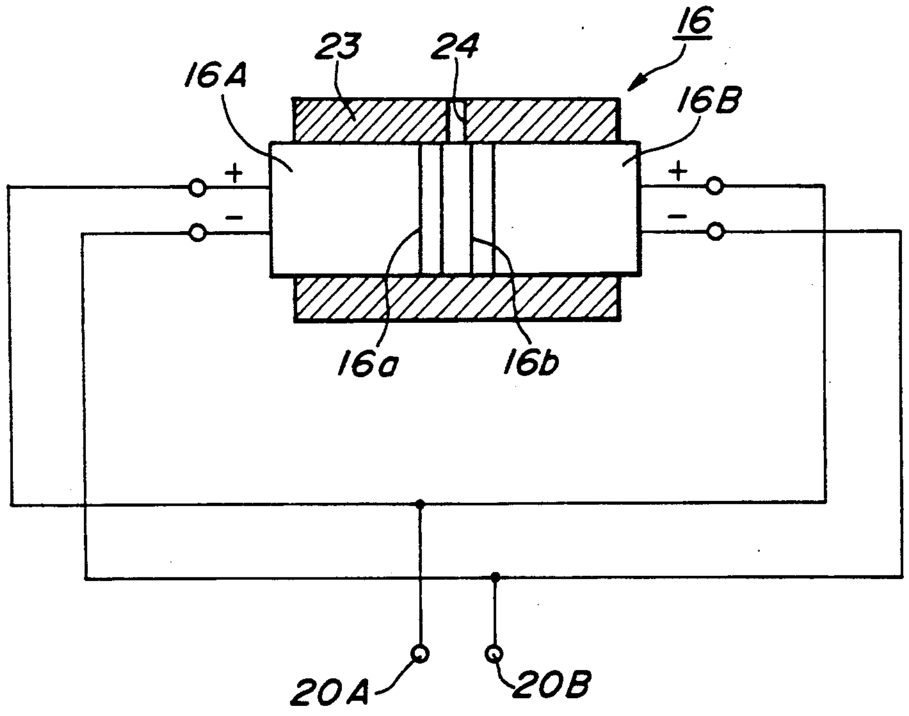
FIG. 6 is a partially sectional and partially schematic diagram of the microphone device shown in FIG. 5.

Referring to FIG. 5, in which a specific embodiment of the microphone device 16 is illustrated, the microphone device 16 is constituted by, for example, a pair of non-directional capacitor microphone units 16A, 16B having their characteristics matched to each other and interconnected by a highly stiff connecting element 23, with the diaphragms 16*a*, 16*b* lying closely adjacent and facing to each other. The connecting element 23 has a plurality of through-holes 24 for transmitting acoustic signals to the diaphragms 16*a*, 16*b* of the microphone units 16A, 16B. As shown in FIG. 6, the microphone device 16 is provided with output terminals 20A, 20B to which the positive and the negative signal output terminals of the microphone units 16A, 16B are connected, respectively, as shown.

With the above described microphone device 16, the diaphragms 16*a*, 16*b* of the microphone units 16A, 16B are thrust and deformed as a function of the sound pressure P of acoustic signals transmitted by way of the through-holes 24 formed in the connecting element 23 to produce corresponding electrical signals which are summed and synthesized in phase to each other so as to be output at output terminals 20A, 20B. Since the microphone units 16A, 16B of the microphone device 16 are interconnected by the connecting element 23, noise vibration components, such as impact vibrations applied to the microphone housing or frictional vibrations applied to connection cords, are converted by the microphone units 16A, 16B into anti-phase electrical signals, which are summed to thereby cancel each other, so that only the electrical signals corresponding to the sound pressure P of the acoustic signal are produced at the output terminals 20A, 20B.

Hence, with the above described headphone device, only the acoustic signals in the vicinity of the headphone unit 4 are converted by the microphone device 16 into corresponding electrical signals, which are supplied to the signal adder 2 by way of the feedback circuit 7.

It is noted that, in the above described headphone device, the transfer functions A, H, M and $\beta$ of the amplifier 3, headphone unit 4, microphone unit 16 and the feedback circuit 7 are set in a range which will satisfy the condition $|AHM\beta| > 1$ when expressed in the frequency domain.

With the use of the above described headphone device, an acoustic signal having the sound pressure level P as shown by the formula (1), that is, an acoustic signal wherein conversion characteristics corresponding to $1/M\beta$ are afforded to the input electrical signal S to compensate for frequency characteristics or distortion and in which the signal level N of the external noise is reduced by $1/AHM\beta$, is produced at signal output terminal 19 resting at an entrance to the acoustic meatus of the headphone wearer.

In the embodiment described above in connection with FIGS. 4–6, the acoustic signals in the vicinity of the headphone unit are converted to in-phase electrical signals by a pair of microphone units having their diaphragms disposed closely adjacent and opposite to each other, while vibrational noises caused by mechanical noises are converted into anti-phase electrical signals, which are summed together and thereby cancelled, so that electrical signals corresponding only to acoustic signals in the vicinity of the headphone unit are produced. The sum of the anti-phase signals is supplied via a feedback circuit to the amplifier which amplifies input electrical signals supplied to the headphone unit. Thus the external noises may always be reduced in a regular manner without being affected by mechanical vibration noise.

In the above described embodiments, the present invention is applied to a headphone device. However, when the present invention is applied to a telephone receiver, the signal level of external noise in the vicinity of an ear piece provided with a speaker unit may also be reduced by $1/AHM\beta$. Accordingly, the acoustic signals containing external noise in the vicinity of the ear piece are converted by the microphone unit into electrical signals, which are negatively fed back via a feedback circuit such that the transfer functions of the amplifier circuit, speaker unit, microphone unit and the feedback circuit are set within the range of $|AHM\beta| > 1$.

Thus a telephone receiver may be provided in which, even in an environment having a high surrounding noise level, the external noise input to the user's ear may be reduced to elevate the S/N ratio of the acoustic output of the speaker unit to enable the voice of the calling party to be heard clearly.

For adjusting the volume of the acoustic signal or output produced at the signal output terminal 19, a sound volume adjustment unit may be provided at the sound source side, that is, upstream of the signal input terminal 1.

What is claimed is:

1. A noise reducing receiver device, comprising;

electro-acoustic transducing means for converting electrical signals into acoustic output signals and having a transfer function H;

amplifying means having a transfer function A for amplifying electrical signals and supplying the amplified electrical signals to said electro-acoustic transducing means;

microphone means for converting output acoustic signals from said electro-acoustic transducing means together with acoustic noise in the vicinity of said electro-acoustic transducing means into electrical signals, said microphone means having a transfer function M and comprising a first microphone means having a first diaphragm and a second microphone means having a second diaphragm, the first and second diaphragms being disposed in mutual proximity and in opposition to each other; and feedback means having a transfer function $\beta$ for negatively feeding back electrical signals produced by said microphone means as an input to said amplifying means, wherein least one of said transfer functions is adjustable within a predetermined range such that $|AHM\beta| > 1$.

2. The noise reducing receiver device according to claim 1, wherein said amplifying means comprises variable gain amplifying means having a gain as said transfer function A which is variably adjustable within a range determined by $|AHM\beta| > 1$.

3. The noise reducing receiver device according to claim 1, wherein the transfer function $\beta$ of said feedback means is adjustable within a range determined by $|AHM\beta| > 1$.

4. The noise reducing receiver device according to claim 1, wherein said electro-acoustic transducing means comprises a headphone.

5. The noise reducing receiver device according to claim 1, wherein said electro-acoustic transducing means comprises a speaker means of a telephone handset.

6. The noise reducing receiver device according to claim 1, wherein said microphone means includes first and second output terminals and each of said first microphone means and said second microphone means is provided with a respective first polarity output terminal and a respective second polarity output terminal, the first polarity output terminals of the first and second microphone means being connected together and to the first output terminal of said microphone means and the second polarity output terminals of the first and second microphone means being connected together and to the second output terminal of said microphone means.

7. The noise reducing receiver device according to claim 1, further comprising connecting means for rigidly interconnecting said first microphone means and said second microphone means.

* * * * *